United States Patent
Matsuda et al.

(10) Patent No.: US 9,498,458 B2
(45) Date of Patent: Nov. 22, 2016

(54) METHOD OF INHIBITING OR TREATING FIBROSIS

(71) Applicant: MediciNova, Inc., La Jolla, CA (US)

(72) Inventors: Kazuko Matsuda, Beverly Hills, CA (US); Yuichi Iwaki, La Jolla, CA (US)

(73) Assignee: MediciNova, Inc., La Jolla, CA (US)

( * ) Notice: Subject to any disclaimer, the term of this patent is extended or adjusted under 35 U.S.C. 154(b) by 0 days.

(21) Appl. No.: 14/726,888

(22) Filed: Jun. 1, 2015

(65) Prior Publication Data

US 2015/0342913 A1     Dec. 3, 2015

Related U.S. Application Data

(60) Provisional application No. 62/006,693, filed on Jun. 2, 2014.

(51) Int. Cl.
*A61K 31/192*     (2006.01)

(52) U.S. Cl.
CPC .................................. *A61K 31/192* (2013.01)

(58) Field of Classification Search
None
See application file for complete search history.

(56) References Cited

U.S. PATENT DOCUMENTS

| | | |
|---|---|---|
| 4,788,055 A | 11/1988 | Fischer et al. |
| 4,816,264 A | 3/1989 | Phillips et al. |
| 4,828,836 A | 5/1989 | Elger et al. |
| 4,834,965 A | 5/1989 | Martani et al. |
| 4,834,985 A | 5/1989 | Elger et al. |
| 4,985,585 A | 1/1991 | Ohashi et al. |
| 4,996,047 A | 2/1991 | Kelleher et al. |
| 5,071,646 A | 12/1991 | Malkowska et al. |
| 5,133,974 A | 7/1992 | Paradissis et al. |
| 5,290,812 A | 3/1994 | Ohashi et al. |
| 7,060,854 B2 | 6/2006 | Locke et al. |
| 7,064,146 B2 | 6/2006 | Locke et al. |
| 8,962,687 B2 * | 2/2015 | Matsuda ............... A61K 31/192 514/571 |
| 2013/0158123 A1 | 6/2013 | Matsuda |

OTHER PUBLICATIONS

Shigeki Tsukada et al., "Mechanisms of liver fibrosis", Cinica Chimica Acta, 2006, vol. 364, pp. 33-60.
International Search Report corresponding to Application No. PCT/US2015/033518, dated Aug. 12, 2015.
International Search Report and Written Opinion issued in corresponding application No. PCT/US15/33518 mailed Aug. 12, 2015.
Cheong, B.Y.C. et al. "Nephrogenic Systemic Fibrosis: A Concise Review for Cardiologists." Texas Heart Institute Journal, vol. 37, No. 5, 2010, pp. 508-515.
Cowper, Shawn E., M.D. Nephrogenic Systemic Fibrosis Case Definition; updated Jun. 15, 2013; Dr. Cowper's NSF Blog; available at www.icnfdr.org (6 pgs.).

* cited by examiner

*Primary Examiner* — Brian J Davis
(74) *Attorney, Agent, or Firm* — Gilberto M. Villacorta; Lydia B. Choi; Foley & Lardner LLP

(57) ABSTRACT

A compound of Formula (I) or a metabolite thereof, or an ester of the compound of Formula (I) or the metabolite thereof, or a pharmaceutically acceptable salt of each thereof, wherein Formula (I), m, n, $X^1$ and $X^2$ are as defined herein, is useful for inhibiting, reducing, or treating fibrosis, conditions leading to or arising from it, and/or negative effects of each thereof.

24 Claims, No Drawings

METHOD OF INHIBITING OR TREATING FIBROSIS

CROSS-REFERENCE TO RELATED APPLICATION

This application claims priority to U.S. provisional application No. 62/006,693 filed Jun. 2, 2014, the content of which is incorporated herein in its entirety by reference.

FIELD

This technology relates to methods of inhibiting, reducing, or treating fibrosis, conditions leading to or arising from it, and/or negative effects of each thereof by administering phenoxyalkylcarboxylic acids such as MN-001 and MN-002.

BACKGROUND

Fibrosis can be generally defined as excessive deposition of extra cellular matrix (ECM) components such as fibronectin (FN) and type I collagen (Col1α1) by organ fibroblasts. Organ fibrosis is the final common pathway for many diseases that result in end-stage organ failure. However, effective therapy for organ fibrosis is unavailable. Uncontrollable wound-healing responses, including acute and chronic inflammation, angiogenesis, activation of resident cells, and ECM remodeling, are thought to be involved in the pathogenesis of fibrosis. TGF-β is a prototype fibrotic cytokine that is increased in fibrotic organs and contributes to the development of fibrosis by stimulating the synthesis of ECM molecules, activating fibroblasts to α smooth muscle actin (α SMA)-expressing myofibroblasts, and downregulating matrix metalloproteinases (MMPs). However, a clinical trial of a monoclonal anti-TGF-β antibody in fibrosis patients, such as those with early secondary sclerosis (SSc), failed to show any efficacy (Varga and Pasche, Nature Reviews Rheumatology 2009; 5:200-6).

SUMMARY

Provided herein are methods for inhibiting, reducing, or treating fibrosis, conditions leading to or arising from it, and/or negative effects of each thereof. The methods include administering a phenoxyalkylcarboxylic acid, non-limiting examples of which include MN-001 and MN-002, or a metabolite thereof, or an ester of each thereof, or a pharmaceutically acceptable salt of each of the above.

In one aspect, a method of inhibiting or treating fibrosis in a patient suffering therefrom is provided, the method including administering to a patient in need thereof an effective amount of a compound of Formula (I):

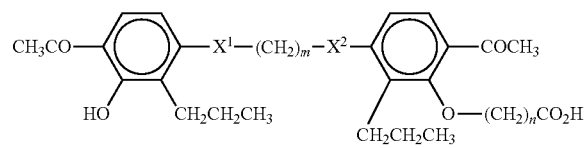

(I)

or a metabolite thereof, or an ester of the compound of Formula (I) or the metabolite thereof, or a pharmaceutically acceptable salt of each thereof, wherein m is an integer from 2 to 5 inclusive, and n is an integer from 3 to 8 inclusive, $X^1$ and $X^2$ each independently represent sulfur, oxygen, a sulfinyl (—S(O)—) group, or a sulfonyl (—S(O)$_2$—) group, provided that $X^1$ and $X^2$ are not simultaneously oxygen.

In another aspect, a method of reducing and/or inhibiting elevated hydroxyproline levels and/or collagen levels in a fibrosis in a patient suffering therefrom is provided. The method includes administering to the patient an effective amount of a compound of Formula (I), or a metabolite thereof, or an ester of the compound of Formula (I) or the metabolite thereof, or a pharmaceutically acceptable salt of each thereof.

In one embodiment, the fibrosis excludes pulmonary fibrosis, such as idiopathic and non-idiopathic pulmonary fibrosis. In one embodiment, the fibrosis excludes hepatic fibrosis provided that the hepatic fibrosis excluded is not viral hepatitis induced fibrosis or alcoholic liver damage induced liver fibrosis. Therefore, in one embodiment, the fibrosis treated, reduced, or inhibited, is viral hepatitis induced fibrosis or alcoholic liver damage induced liver fibrosis.

In some embodiments, the fibrosis inhibited or treated is one or more of: aberrant wound healing, alcoholic liver damage induced liver fibrosis, bridging fibrosis, Crohn's Disease (fibrosis of the intestine), cystic fibrosis of the pancreas and lungs, injection fibrosis, which can occur as a complication of intramuscular injections, especially in children, endomyocardial fibrosis or cardiac fibrosis (fibrosis of the heart), fibrosis resulting from of Graft-Versus-Host Disease (GVHD), fibrosis of the spleen, fibrosis of the eye including subretinal fibrosis, fibrotic complications of surgery or injection fibrosis, glomerulonephritis, interstitial fibrosis, keloid and hypertrophic scar (fibrosis of the skin), macular degeneration, mediastinal fibrosis (fibrosis of the soft tissue of the mediastinum), morphea, multifocal fibrosclerosis, myelofibrosis (fibrosis of the bone marrow), nephrogenic systemic fibrosis (fibrosis of the skin), nodular subepidermal fibrosis (e.g, benign fibrous histiocytoma, pleural fibrosis, fibrosis as a consequence of surgery (e.g., surgical implants), proliferative fibrosis, pipestem fibrosis, postfibrinous fibrosis, progressive massive fibrosis (a type of fibrosis of the lungs, a complication of coal workers' pneumoconiosis), old myocardial infarction (fibrosis of the heart), pancreatic fibrosis, progressive massive fibrosis, radiation fibrosis, renal fibrosis, renal fibrosis related to or arising from chronic kidney disease, retroperitoneal fibrosis (fibrosis of the soft tissue of the retroperitoneum), scarring after surgery, scleroderma/systemic sclerosis (fibrosis of the skin), subepithelial fibrosis, uterine fibrosis, and viral hepatitis induced fibrosis.

In one embodiment, the compound of Formula (I) is a compound of Formula (IA) (or MN-001):

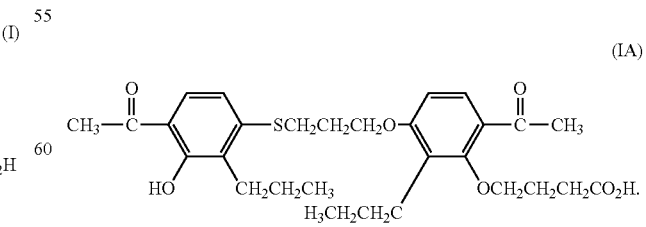

(IA)

In another embodiment, the metabolite of the compound of Formula (I) and (IA) is a compound of Formula (IB) (or MN-002):

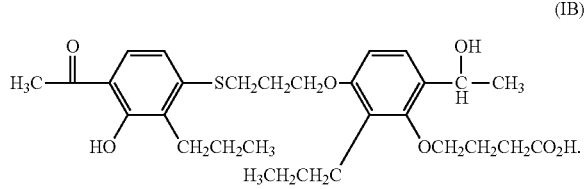

(IB)

DETAILED DESCRIPTION

Definitions

As used herein, and in the appended claims, the singular forms "a," "an" and "the" include plural references unless the context clearly dictates otherwise.

"Administering" or "Administration of" a drug to a patient (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

"$C_X$" when placed before a group refers to the number of carbon atoms in that group to be X.

"Alkyl" refers to a monovalent acyclic hydrocarbyl radical having 1 to-12 carbon atoms. Non limiting examples of alkyl include methyl, ethyl, propyl, isopropyl, butyl, isobutyl, tertiary butyl, pentyl, hexyl and the like.

"Aryl" refers to a monovalent aromatic hydrocarbyl radical having up to 10 carbon atoms. Non-limiting examples of aryl include phenyl and naphthyl.

"Heteroaryl" refers to an aromatic group of from 1 to 10 carbon atoms and 1 to 4 heteroatoms selected from the group consisting of oxygen, nitrogen, sulfur within the aromatic ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Non limiting examples of heteroaryl include pyridyl, pyrrolyl, indolyl, thiophenyl, and furyl.

"Cycloalkyl" refers to a monovalent non-aromatic cyclic hydrocarbyl radical having 3-12 carbon atoms. Non limiting examples of cycloalkyl include cyclopropyl, cyclobutyl, cyclopentyl, cyclohexyl, and the like.

"Heterocyclyl" refers to a monovalent non-aromatic cyclic group of 1 to 10 carbon atoms and 1 to 4 heteroatoms selected from the group consisting of oxygen, nitrogen, sulfur within the cycle, wherein the nitrogen and/or sulfur atom(s) of the heteroaryl are optionally oxidized (e.g., N-oxide, —S(O)— or —S(O)$_2$—). Such heteroaryl groups can have a single ring (e.g., piperidinyl or tetrahydrofuranyl) or multiple condensed rings wherein the condensed rings may or may not be aromatic and/or contain a heteroatom provided that the point of attachment is through an atom of the non-aromatic heterocyclyl group. Non limiting examples of heterocyclyl include pyrrolidinyl, piperidinyl, piperazinyl, and the like.

"Amino" refers to —NH$_2$.

"Alkylamino" refers to —NHR$_B$, wherein R$_B$ is C$_1$-C$_6$ alkyl optionally substituted with 1-3 aryl, heteroaryl, cycloalkyl, or heterocyclyl group.

"Dialkylamino" refers to —N(R$_B$)$_2$, wherein R$_B$ is defined as above.

"Comprising" shall mean that the methods and compositions include the recited elements, but not exclude others. "Consisting essentially of" when used to define methods and compositions, shall mean excluding other elements of any essential significance to the combination for the stated purpose. Thus, e.g., a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transitional terms and phrases are within the scope of this invention.

"Effective amount" of a compound utilized herein is an amount that, when administered to a patient treated as herein, will have the intended therapeutic effect, e.g., alleviation, amelioration, palliation or elimination of one or more manifestations of the medical condition in the patient. The full therapeutic effect does not necessarily occur by administration of one dose (or dosage), and may occur only after administration of a series of doses. Thus, an effective amount may be administered in one or more administrations.

"Fibrosis" or "fibrogenesis" refers to a formation of excess fibrous connective tissue in an organ or tissue, e.g., in a reparative or reactive process. This is as opposed to formation of fibrous tissue as a normal constituent of an organ or tissue. In the present technology, the term "fibrosis" is used to distinguish abnormal from normal healing processes. Fibrogenesis or fibrisos is the process of forming fibrous tissue usually by degeneration (e.g., fibrosis of the pulp) and a proliferation of fibroblasts. Scarring is confluent fibrosis that obliterates the architecture of the underlying organ or tissue. Examples of fibrosis include, without limitation, aberrant wound healing, alcoholic liver damage induced liver fibrosis, bridging fibrosis, Crohn's Disease (fibrosis of the intestine), cystic fibrosis of the pancreas and lungs, injection fibrosis, which can occur as a complication of intramuscular injections, especially in children, endomyocardial fibrosis or cardiac fibrosis (fibrosis of the heart), fibrosis resulting from of Graft-Versus-Host Disease (GVHD), fibrosis of the spleen, fibrosis of the eye including subretinal fibrosis, fibrotic complications of surgery or injection fibrosis, glomerulonephritis, interstitial fibrosis, keloid and hypertrophic scar (fibrosis of the skin), macular degeneration, mediastinal fibrosis (fibrosis of the soft tissue of the mediastinum), morphea, multifocal fibrosclerosis, myelofibrosis (fibrosis of the bone marrow), nephrogenic systemic fibrosis (fibrosis of the skin), nodular subepidermal fibrosis (e.g, benign fibrous histiocytoma, pleural fibrosis, fibrosis as a consequence of surgery (e.g., surgical implants), proliferative fibrosis, pipestem fibrosis, postfibrinous fibrosis, progressive massive fibrosis (a type of fibrosis of the lungs, a complication of coal workers' pneumoconiosis), old myocardial infarction (fibrosis of the heart), pancreatic fibrosis, progressive massive fibrosis, radiation fibrosis, renal fibrosis, renal fibrosis related to chronic kidney disease, retroperitoneal fibrosis (fibrosis of the soft tissue of the retroperitoneum), scarring after surgery, scleroderma/systemic sclerosis (fibrosis of the skin), subepithelial fibrosis, uterine fibrosis, and viral hepatitis induced fibrosis.

Mechanistically, and without being bound by theory, excessive deposition of ECM components such as fibronectin (FN) and type I collagen (Col1α1) by organ fibroblasts can leasd to fibrosis. Organ fibrosis is a final common pathway for many diseases that result in end-stage organ failure. Uncontrollable wound-healing responses, including acute and chronic inflammation, angiogenesis, activation of resident cells, and ECM remodeling are contemplated to be involved in the pathogenesis of fibrosis. TGF-β is a fibrotic cytokine that is increased in fibrotic organs and contributes to the development of fibrosis by stimulating the synthesis of ECM molecules, activating fibroblasts to α-smooth muscle actin (α-SMA)-expressing myofibroblasts, and downregulating matrix metalloproteinases (MMPs).

"Pharmaceutically acceptable" refers to non-toxic and suitable for administration to a patient, including a human patient.

"Pharmaceutically acceptable salts" refer to salts that are non-toxic and are suitable for administration to patients. Non-limiting examples include alkali metal, alkaline earth metal, and various primary, secondary, and tertiary ammonium salts. When the ester of the compound of Formula (I) includes a cationic portion, for example, when the ester includes an amino acid ester, the salts thereof can include various carboxylic acid, sulfonic acid, and miner acid salts. Certain non-limiting examples of salts include sodium, potassium, and calcium salts.

"Protecting groups" refer to well-known functional groups which, when bound to a functional group, render the resulting protected functional group inert to the reaction to be conducted on other portions of a compound and the corresponding reaction condition, and which can be reacted to regenerate the original functionality under deprotection conditions. The protecting group is selected to be compatible with the remainder of the molecule. A "carboxylic acid protecting group" protects the carboxylic functionality of the phenoxyalkylcarboxylic acids during their synthesis. Non limiting examples of carboxylic acid protecting groups include, benzyl, p-methoxybenzyl, p-nitrobenzyl, allyl, benzhydryl, and trityl. Additional examples of carboxylic acid protecting groups are found in standard reference works such as Greene and Wuts, Protective Groups in Organic Synthesis, 2d Ed., 1991, John Wiley & Sons, and McOmie Protective Groups in Organic Chemistry, 1975, Plenum Press. Methods for protecting and deprotecting the carboxylic acids disclosed herein can be found in the art, and specifically in Greene and Wuts, supra, and the references cited therein.

"Treating" a medical condition or a patient refers to taking steps to obtain beneficial or desired results, including clinical results. For purposes of the various aspects and embodiments of the present invention, beneficial or desired clinical results include, but are not limited to, reduction, alleviation, or amelioration of one or more manifestations of or negative effects of pulmonary fibrosis, improvement in one or more clinical outcomes, diminishment of extent of fibrosis, delay or slowing of fibrosis progression, amelioration, palliation, or stabilization of the fibrosis state, and other beneficial results described herein.

Provided herein are methods administering an effective amount of a compound of Formula (I):

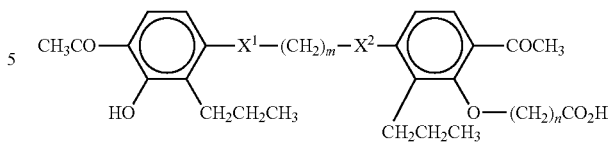

(I)

or a metabolite thereof, or an ester of the compound of Formula (I) or the metabolite thereof, or a pharmaceutically acceptable salt of each thereof, wherein the variables are defined as herein.

As used herein, "a metabolite thereof" refers to a metabolite that shows substantially similar therapeutic activity as a compound of Formula (I). Non limiting examples of such metabolites include compounds where the —COCH$_3$ group, of a compound of Formula (I), that is attached to the phenyl containing the —O—(CH$_2$)$_n$CO$_2$H moiety is metabolized to a 1-hydroxyethyl (i.e. —CH(OH)Me) group.

Metabolites containing a 1-hydroxyethyl group contain an asymmetric center on the 1-position of the 1-hydroxyethyl group. The corresponding enantiomers and mixtures thereof, including racemic mixtures, are included within the metabolites of the compound of Formula (I) as utilized herein.

As used herein, "an ester thereof" refers to an ester of the phenolic hydroxy group and/or an ester of the carboxylic acid shown in the compound of Formula (I), and an ester of the 1-hydroxyethyl (an aliphatic hydroxy group) group of a metabolite of the compound Formula (I). An ester of the phenolic and/or the aliphatic hydroxy groups can include, without limitation, as the corresponding acid, a carboxylic acid R$_A$—CO$_2$H, wherein R$_A$ is C$_1$-C$_6$ alkyl, aryl, heteroaryl, C$_3$-C$_{12}$ cycloalkyl, or C$_2$-C$_8$ heterocyclyl, wherein the alkyl, aryl, heteroaryl, cycloalkyl, or heterocyclyl are optionally substituted with from 1 to 4 C$_1$-C$_3$ alkyl, aryl, CO$_2$H, amino, alkylamino, or dialkylamino groups. Other acids such as mono-, di-, or tri phosphoric acids are also contemplated. An ester of the carboxylic acid can include, without limitation, as the corresponding alcohol, a compound of formula R$_A$—OH, wherein R$_A$ is defined as above. In one embodiment, only the carboxylic acid in Formula (I) is esterified. In another embodiment, only the phenolic hydroxy group in Formula (I) is esterified. In another embodiment, R$_A$ is C$_1$-C$_4$ alkyl. As will be apparent to the skilled artisan, such esters act as prodrugs that are hydrolyzed in vivo to release the compound of Formula (I) or a salt thereof.

In an embodiment, the compound of Formula (I) is a compound of Formula (IA):

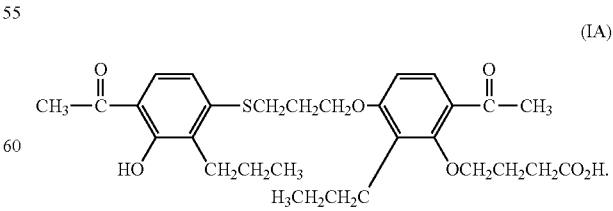

(IA)

In another embodiment, the metabolite of the compound of Formula (I) and (IA) is a compound of Formula (IB):

(IB)

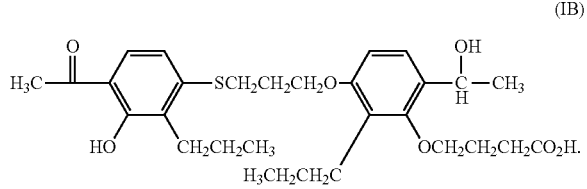

In another embodiment, the compound is administered orally. In another embodiment, the compound is administered as a tablet or a capsule. In another embodiment, the compound of Formula (IA) is present in polymorphic form A that is substantially free of other polymorphic forms. In another embodiment, the compound is administered as a liquid dosage form. In another embodiment, the compound is administered in an amount from about 100 to about 4,000 mg/day, divided into one, two, or three portions.

The efficacy of a compound utilized herein can be tested by methods well known to the skilled artisan, such as those illustrated in the Examples section.

Synthesis

The synthesis and certain biological activity of the compounds of Formula (I) are described in U.S. Pat. No. 4,985,585 which is incorporated herein in its entirety by reference. For example, the compound of Formula (IA) is prepared by reacting a phenol of Formula (II):

(II)

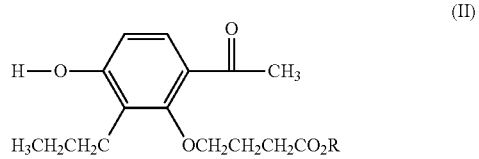

wherein, R is a carboxylic acid protecting group, with a compound of Formula (III):

(III)

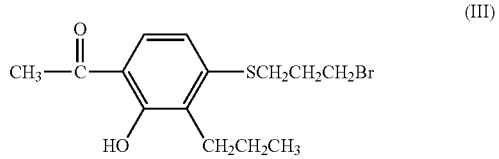

to provide a compound of Formula (IC):

(IC)

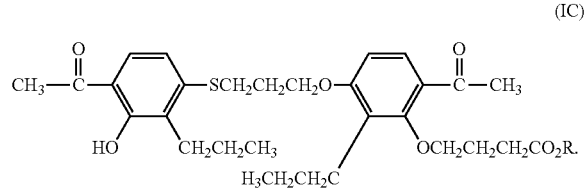

Non-limiting examples of acid protecting groups, or R groups, include $C_1$-$C_6$ alkyl, benzyl, benzhydryl, and trityl, wherein the benzyl, benzhydryl, or trityl group is optionally substituted with from 1 to 6 $C_1$-$C_6$ alkyl, halo, and/or $C_1$-$C_6$ alkoxy groups. It will be apparent to the skilled artisan that a leaving group other than the bromo group of Formula (III) may be used. Non-limiting examples of such other leaving groups include chloro or tosylate.

De-protection of the protected carboxylic acid of Formula (IC) provides the compound of Formula (IA). As is apparent based on this disclosure, compounds of Formula (IC) are in some embodiments useful in accordance with this invention. Non-limiting examples of deprotection methods include, alkaline hydrolysis and hydrogenolysis under $H_2$ and a catalyst such as Pd/C or Pt/C.

The reactions are carried out in an inert organic solvent, for example and without limitation, acetone, methylethylketone, diethylketone, or dimethylformamide. The nucleophilic displacement reaction may be conducted at a temperature below room temperature up to the reflux temperature of the solvent, in the presence of an inorganic base, such as potassium carbonate or sodium carbonate, and optionally in the presence of potassium iodide. The reactions are carried out for a period of time sufficient to provide substantial product as determined by well-known methods such as thin layer chromatography and $^1$H-NMR. Other compounds utilized herein are made by following the procedures described herein and upon appropriate substitution of starting materials, and/or following methods well known to the skilled artisan. See also, U.S. Pat. No. 5,290,812 (incorporated herein in its entirety by reference).

The compound of Formula (IA) is recrystallized under controlled conditions to provide an essentially pure orthorhombic polymorph, referred to as Form A crystals (e.g., 90% or more, preferably at least 95% Form A). Polymorphic Form A and processes for producing it are described in U.S. Pat. Nos. 7,060,854 and 7,064,146; which are incorporated herein in their entirety by reference. All polymorphic forms of the compound of Formula (I) are active, but polymorphic Form A is preferred. Under certain conditions, the solubility and the bioavailability of this polymorph are superior to the other polymorphs, and, thus, Form A may offer improved solid formulations.

Form A crystals can be obtained, For example, by dissolving the compound of Formula (IA) in 5 to 10 parts by weight of ethanol at 25° C. to 40° C. to give a yellow to orange solution. The ethanol solution is charged with 1 to 10 parts of water and agitated at 20° C. to 25° C. for about 15 to 60 minutes and then at 5° C. to 10° C. for an additional period of from 1 to 4 hours, preferably 2.0 to 3.0 hours, resulting in an off-white suspension. To this suspension is added 5 to 15 parts of water and the mixture is agitated at 5 to 10° C. for an additional from 1 to 4 hours, preferably 1.5 to 2.0 hours. A solid, white to off-white product is isolated by vacuum filtration and the filter cake is washed with water and dried in a vacuum at 25° C. to 40° C. for 12 to 24 hours.

For compounds utilized herein that exist in enantiomeric forms, such as certain metabolites of the compound of Formula (I) (for example, the compound of formula IB), the two enantiomers can be optically resolved. Such a resolution is performed, for example, and without limitation, by forming diastereomeric salt of a base such as (S)-(−)-1-(1-naphthyl) ethylamine with the corresponding carboxylic acid compound, or by separating the enantiomers using chiral column chromatography. Intermediates to such compounds, which intermediates also exist in enantiomeric forms can be similarly resolved.

Administration and Formulation

The compounds utilized herein can be administered orally, or by intravenous, intramuscular, and subcutaneous injection, or transdermal methods. Effective dosage levels can vary widely, e.g., from about 100 to about 4000 mg per day. In one embodiment, the daily dosage range is 250 to 2,000 mg, given in one, two or three portions. In one embodiment, the daily dosage range is 100 to 500 mg, such as 100, 200, 300, 400, or 500 mg given in one, two or three portions. In one embodiment, the daily dosage range is 250 to 2,000 mg, such as 250, 500, 750, 1,000, 1,250, 1,500, 1,750, or 2,000 mg given in one, two or three portions. In one embodiment, the daily dosage range is 1000 to 4,000 mg, such as 1,000, 2,000, 3,000, or 4,000 mg, given in one, two or three portions. In another embodiment, the dosage is 1000 mg twice a day. In other embodiments, suitable dosages include 1000 mg qd, 1000 mg bid, and 750 mg tid.

Actual amounts will depend on the circumstances of the patient being treated. As those skilled in the art recognize, many factors that modify the action of the active substance will be taken into account by the treating physician such as the age, body weight, sex, diet and condition of the patient, the time of administration, the rate and route of administration. Optimal dosages for a given set of conditions can be ascertained by those skilled in the art using conventional dosage determination tests.

The compounds utilized herein can be formulated in any pharmaceutically acceptable form, including liquids, powders, creams, emulsions, pills, troches, suppositories, suspensions, solutions, and the like. Therapeutic compositions containing the compounds utilized herein will ordinarily be formulated with one or more pharmaceutically acceptable ingredients in accordance with known and established practice. In general, tablets are formed utilizing a carrier such as modified starch, alone or in combination with carboxymethyl cellulose (Avicel), for example at about 10% by weight. The formulations are compressed at from 1,000 to 3,000 pounds pressure in the tablet forming process. The tablets preferably exhibit an average hardness of about 1.5 to 8.0 kp/cm$^2$, preferably 5.0 to 7.5 kp/cm$^2$. Disintegration time varies from about 30 seconds to about 15 or 20 minutes.

Formulations for oral use can be provided as hard gelatin capsules wherein the therapeutically active compounds utilized herein are mixed with an inert solid diluent such as calcium carbonate, calcium phosphate or kaolin, or as soft gelatin capsules in which the compounds are mixed with an oleaginous medium, e.g., liquid paraffin or olive oil. Suitable carriers include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like.

The compounds utilized herein can be formulated as aqueous suspensions in admixture with pharmaceutically acceptable excipients such as suspending agents, e.g., sodium carboxymethyl cellulose, methylcellulose, hydroxypropylmethyl cellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g, heptadecaethylene-oxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl- or n-propyl-p-hydroxy benzoate, one or more coloring agents, one or more flavoring agents and one or more sweetening agents, such as glycerol, sorbitol, sucrose, saccharin or sodium or calcium cyclamate.

Suitable formulations also include sustained release dosage forms, such as those described in U.S. Pat. Nos. 4,788,055; 4,816,264; 4,828,836; 4,834,965; 4,834,985; 4,996,047; 5,071,646; and, 5,133,974, the contents of which are incorporated herein in their entirety by reference.

Other forms suitable for oral administration include liquid form preparations including emulsions, syrups, elixirs, aqueous solutions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Solid form preparations may contain, in addition to the active component, colorants, flavors, stabilizers, buffers, artificial and natural sweeteners, dispersants, thickeners, solubilizing agents, and the like.

The compounds utilized herein may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example as solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds utilized herein may be formulated for nasal administration. The solutions or suspensions are applied directly to the nasal cavity by conventional means, for example, with a dropper, pipette or spray. The formulations may be provided in a single or multidose form. The patient can administer an appropriate, predetermined volume of the solution or suspension via a dropper or pipette. A spray may be administered for example by means of a metering atomizing spray pump.

The compounds utilized herein may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine. The powder carrier will form a gel in the nasal cavity. The powder composition may be presented in unit dose form for example in capsules or cartridges of, for example gelatin or blister packs from which the powder may be administered by means of an inhaler.

The compounds utilized herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges including active agents in a flavored base, usually sucrose and acacia or tragacanth; pastilles including the active ingredient in an inert base such as gelatin and glycerin or sucrose and acacia; and mouthwashes including the active ingredient in a suitable liquid carrier.

The compounds utilized herein may be formulated for administration as suppositories. In such a formulation, a low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds utilized herein may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. A common type of controlled release formulation that may be used for the purposes of the present invention comprises an inert core, such as a sugar sphere, a first layer, coated with an inner drug-containing second layer, and an outer membrane or third layer controlling drug release from the inner layer.

The cores are preferably of a water-soluble or swellable material, and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose.

The substantially water-insoluble material in the first layer is generally a "GI insoluble" or "GI partially insoluble" film forming polymer (dispersed or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone, polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethyl hydroxyethyl cellulose, acrylic acid polymers, polymethacrylates, or any other pharmaceutically acceptable polymer. The ratio of drug to hydrophilic polymer in the second layer is usually in the range of from 1:100 to 100:1 (w/w).

Suitable polymers for use in the third layer, or membrane, for controlling the drug release may be selected from water insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above.

Optionally, the controlled release layer comprises, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

Also provided herein are unit dosage forms of the formulations. In such forms, the formulation is subdivided into unit dosages containing appropriate quantities of the active component (e.g., and without limitation, a compound of Formula (I) or an ester thereof, or a salt of each thereof). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa.

The present invention, thus generally described, will be understood more readily by reference to the following examples, which are provided by way of illustration and are not intended to be limiting of the present invention.

EXAMPLES

The following tests can be employed for demonstrating the therapeutically beneficial effects of MN-001, MN-002, or another compound utilized herein (collective "a compound utilized herein") in fibrosis. In the studies presented herein, the effects of a compound utilized herein on fibrosis are evaluated.

Example 1

The effect of a compound utilized herein on fibrosis is assessed in vitro using primary human fibroblasts, ex vivo using human skin, and in vivo in mice skin treated with TGF-$\beta$.

Materials and Methods

Primary fibroblast culture: Human primary skin fibroblasts are cultured. The clinically involved skin of SSc patients, a morphea patient and healthy donors are used for primary fibroblast culture. Approximately 2-cm pieces of peripheral and skin are minced and fibroblasts are cultured in Dulbecco's modified Eagle's medium supplemented with 10% FBS, penicillin, streptomycin, and anti-mycotic agent, as previously described. The cells are used between passages 3-6.

Ex Vivo Human Skin Assays

Human abdominal skin is obtained from corrective plastic surgery. Subcutaneous fat tissue is removed uniformly and skin tissue is cut into 1.5 cm×1.5 cm sections. The following are injected intradermally: a compound utilized herein, a compound utilized herein in combination with TGF-β (10 ng/ml), and TGF-β alone (10 ng/ml). In some experiments, human skin is first injected with TGF-β for 48 h followed by administration of a compound utilized herein in the same injection site as TGF-β. Independent experiments are conducted in duplicate or triplicate. Explants containing complete epidermal and dermal layers are cultured in an air liquid interface with the epidermal and keratin layers side up and exposed to air. The culture medium is replaced every other day. After 1 or 2 weeks, skin tissue corresponding to an area with 8-mm diameter centered around the injection site is harvested using disposable 8-mm ACUPUNCH® (Acuderm Inc., Lauderdale, Fla.) Skin tissue is fixed in 10% formalin prior to embedding in paraffin.

In Vivo Mouse Experiments

CB57BL6/J male mice are purchased from The Jackson Laboratory (Bar Harbor, Me.). A compound utilized herein alone or in combination with TGF-β (10 ng/ml), or TGF-β alone are injected intradermally on the back of mice. Mice are injected in two different skin sites and sacrificed one week post-injection. Skin surrounding the injection site is harvested and fixed in 10% formalin prior to embedding in paraffin.

Measurement of Skin Dermal Thickness

Six μm sections of paraffin-embedded human and mouse skin tissues are stained with hematoxylin and eosin (H&E). In some experiments, sections are stained with Masson trichrome which identifies collagens. Images are taken on a Nikon Eclipse 800 microscope. The thickness of the dermis is measured in 6 random fields of each section using the image/J® software.

Statistical Analysis

All continuous variables ere expressed as the mean+/− standard deviation. Comparisons between 2 groups are tested for statistical significance using the paired t-test or Mann-Whitney U test as appropriate. Comparison among 3 groups is performed using ANOVA followed by Bonferroni's test.

Example 1A

Primary fibroblasts obtained from the skin of healthy controls, patients with SSc or localized scleroderma (morphea) are treated with a compound utilized herein.

Example 1B

Myofibroblasts, activated fibroblasts which express α-SMA, are induced by TGF-β stimulation and play a role in fibrosis. Subsequently, the effects of a compound utilized herein on α-SMA expression in normal skin fibroblasts are examined.

Example 1C

Cultured human skin explants can be used as an organ model to assess the effects of fibrogenic factors and for evaluating the efficacy of inhibitors/therapies to halt the progression of fibrosis and potentially reverse it. To evaluate the efficacy of a compound utilize herein as a potential therapeutic agent for fibrosis, an ex vivo human skin model is used. Since TGF-β can act as a pro-fibrotic factor that plays a central role in fibrosis, human recombinant TGF-β is first injected intradermally to assess the level of fibrosis. TGF-β injection can increase dermal thickness in a dose-dependent manner one week post-injection. The fibrotic effect of TGF-β (10 ng/ml) resolves by two weeks. The baseline effects of a compound utilized herein are examined individually.

Example 1D

The anti-fibrotic effect of a compound utilize herein is further assessed in vivo. A compound utilized herein in combination with TGF-β are injected in the skin of mice, and the dermal thickness in mouse skin is measured over time.

Example 1E

The efficacy of a compound utilized herein is confirmed in pre-clinical models of fibrosis: a) bleomycin-induced dermal fibrosis in vivo in mouse skin and b) TGF-β induced dermal fibrosis in mouse skin. A compound utilized herein or a control compound are administered at the same time as TGF-β or bleomycin or 3-4 days following TGF-β or bleomycin. Mice are sacrificed one and two weeks after TGF-β-initiation of dermal fibrosis, and two to three weeks after bleomycin-induced fibrosis. of the a compound utilized herein are administered intraperitoneally. For these studies, fibrosis is assessed by measuring dermal thickness on H&E skin sections, assessment of collagen levels by Masson Trichrome staining.

Example 2

Tsk Mice Model for Scleroderma

The collagen content and thickness of a subcutaneous fibrous layer are measured in the skin of Tsk mice (Rheum. Dis. Clin. North Am. 16, 153, 1990), and compared with the control mice (pallid mice) at the ages of 5, 10, and 20 weeks (n=6). The collagen content is determined by measuring hydroxyproline, the marker for collagen, using HPLC. Fibrous layer thickness is determined by histological analysis with Azan staining followed by measuring the area of the fibrous layer using an image analysis system.

Effect of a Compound Utilized Herein Against Tsk Mice Model for Scleroderma 13-week old Tsk mice (n=5) are intraperitoneally administered a compound utilized herein, for example in a dosage of 10 mg-100 mg/kg once daily, such as 10 mg/kg once daily, 30 mg/kg once daily, or 100 mg/kg once daily, for 2 weeks. Five hours after the final administration, the degree of hypertrophy of the subcutaneous fibrous layer are measured and compared with the values of the group administered saline.

Example 3

Measuring Hydroxyproline Levels in Fibrotic Tissue

To quantify lung hydroxyproline content, tissue samples (e.g. and without limitation, 15-25 mg) are processed by an alkaline-acid hydrolysis method as follows. Tissue samples are acid-hydrolyzed with 400 µL of 6N HCl at 121° C. for 20 minutes, and neutralized with 400 µL of 4N NaOH containing 10 mg/mL activated carbon. AC buffer (2.2M acetic acid/0.48M citric acid, 400 µL) is added to the samples, followed by centrifugation to collect the supernatant. A standard curve of hydroxyproline is constructed with serial dilutions of trans-4-hydroxy-L-proline (Sigma-Aldrich, USA) starting at 16 µg/mL. The prepared samples and standards (each 400 µL) are mixed with 400 µL chloramine T solution (Wako Pure Chemical Industries Japan) and incubated for 25 minutes at room temperature. The samples are then mixed with Ehrlich's solution (400 µL) and heated at 65° C. for 20 minutes to develop the color. After samples are cooled on ice and centrifuged to remove precipitates, the optical density of each supernatant is measured at 560 nm. The concentrations of hydroxyproline are calculated from the hydroxyproline standard curve.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of inhibiting or treating fibrosis in a patient suffering therefrom, the method comprising: administering to the patient an effective amount of a compound of Formula (I), a metabolite of the compound of Formula (I), an ester of the compound of Formula (I), or a metabolite of the ester of the compound of Formula (I), or a pharmaceutically acceptable salt of each thereof:

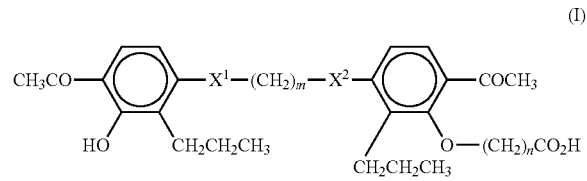

(I)

wherein: m is an integer from 2 to 5, inclusive; n is an integer from 3 to 8, inclusive; and $X^1$ and $X^2$ each independently represent sulfur, oxygen, a sulfinyl group, or a sulfonyl group, provided that $X^1$ and $X^2$ are not simultaneously oxygen;

wherein: the fibrosis excludes (a) pulmonary fibrosis and (b) excludes hepatic fibrosis provided that the hepatic fibrosis excluded is not viral hepatitis induced fibrosis or alcoholic liver damage induced liver fibrosis.

2. The method of claim 1, wherein the compound of Formula (I) is of Formula (IA)

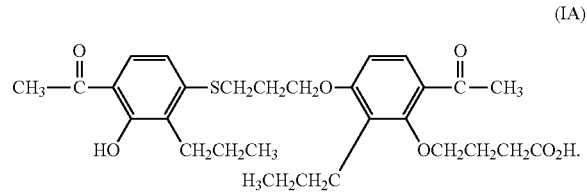

(IA)

3. The method of claim 1, wherein the metabolite of the compound of Formula (I) is a compound of Formula (IB):

(IB)

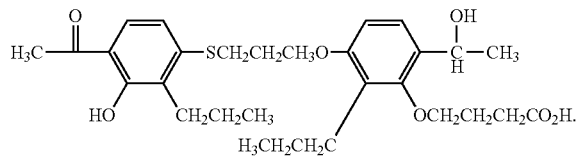

4. The method of claim 1, wherein the compound is administered orally.

5. The method of claim 4, wherein the compound is administered as a tablet or a capsule.

6. The method of claim 2, wherein the compound is present in an orthorhombic polymorphic form A.

7. The method of claim 1, wherein the compound is administered as a liquid dosage form.

8. The method of claim 1, wherein the compound is administered in an amount from about 100 to about 4,000 mg/day, divided into one, two, or three portions.

9. A method of inhibiting or treating a fibrosis in a patient suffering therefrom, the method comprising: administering to the patient an effective amount of a compound of Formula (I), a metabolite of the compound of Formula (I), an ester of the compound of Formula (I), or a metabolite of the ester of the compound of Formula (I), or a pharmaceutically acceptable salt of each thereof:

(I)

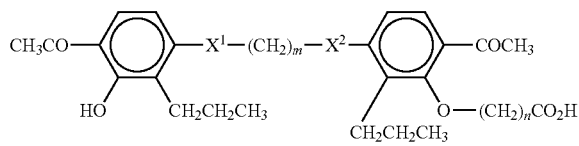

wherein: m is an integer from 2 to 5, inclusive; n is an integer from 3 to 8, inclusive; and $X^1$ and $X^2$ each independently represent sulfur, oxygen, a sulfinyl group, or a sulfonyl group, provided that $X^1$ and $X^2$ are not simultaneously oxygen;

wherein: the fibrosis is selected from aberrant wound healing, alcoholic liver damage induced liver fibrosis, bridging fibrosis, Crohn's Disease (fibrosis of the intestine), cystic fibrosis of the pancreas and lungs, injection fibrosis, endomyocardial fibrosis or cardiac fibrosis (fibrosis of the heart), fibrosis resulting from of Graft-Versus-Host Disease (GVHD), fibrosis of the spleen, fibrosis of the eye, glomerulonephritis, interstitial fibrosis, keloid and hypertrophic scar (fibrosis of the skin), macular degeneration, mediastinal fibrosis (fibrosis of the soft tissue of the mediastinum), morphea, multifocal fibrosclerosis, myelofibrosis (fibrosis of the bone marrow), nephrogenic systemic fibrosis (fibrosis of the skin), nodular subepidermal fibrosis, pleural fibrosis, fibrosis as a consequence of surgery, proliferative fibrosis, pipestem fibrosis, postfibrinous fibrosis, progressive massive fibrosis (a type of fibrosis of the lungs, a complication of coal workers' pneumoconiosis), old myocardial infarction (fibrosis of the heart), pancreatic fibrosis, progressive massive fibrosis, radiation fibrosis, renal fibrosis, renal fibrosis related to or arising from chronic kidney disease, retroperitoneal fibrosis (fibrosis of the soft tissue of the retroperitoneum), scarring after surgery, scleroderma/systemic sclerosis (fibrosis of the skin), subepithelial fibrosis, uterine fibrosis, and viral hepatitis induced fibrosis.

10. The method of claim 9, wherein the compound of Formula (I) is of Formula (IA)

(IA)

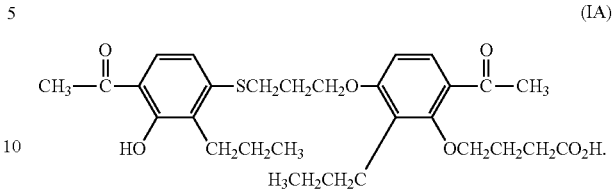

11. The method of claim 9, wherein the metabolite of the compound of Formula (I) is a compound of Formula (IB):

(IB)

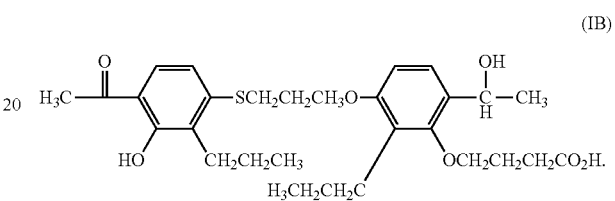

12. The method of claim 9, wherein the compound is administered orally.

13. The method of claim 12, wherein the compound is administered as a tablet or a capsule.

14. The method of claim 10, wherein the compound is present in an orthorhombic polymorphic form A.

15. The method of claim 9, wherein the compound is administered as a liquid dosage form.

16. The method of claim 9, wherein the compound is administered in an amount from about 100 to about 4,000 mg/day, divided into one, two, or three portions.

17. A method of reducing and/or inhibiting elevated hydroxyproline levels in a fibrosis in a patient suffering therefrom, the method comprising administering to the patient an effective amount of a compound of Formula (I), a metabolite of the compound of Formula (I), an ester of the compound of Formula (I), or a metabolite of the ester of the compound of Formula (I), or a pharmaceutically acceptable salt of each thereof:

(I)

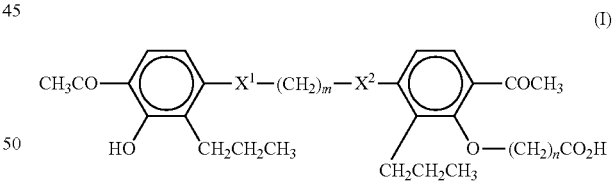

wherein: m is an integer from 2 to 5 inclusive, n is an integer from 3 to 8 inclusive, and $X^1$ and $X^2$ each independently represent sulfur, oxygen, a sulfinyl group, or a sulfonyl group, provided that $X^1$ and $X^2$ are not simultaneously oxygen;

wherein: the fibrosis is selected from: aberrant wound healing, alcoholic liver damage induced liver fibrosis, bridging fibrosis, Crohn's Disease (fibrosis of the intestine), cystic fibrosis of the pancreas and lungs, injection fibrosis, endomyocardial fibrosis or cardiac fibrosis (fibrosis of the heart), fibrosis resulting from of Graft-Versus-Host Disease (GVHD), fibrosis of the spleen, fibrosis of the eye glomerulonephritis, interstitial fibrosis, keloid and hypertrophic scar (fibrosis of the skin), macular degeneration, mediastinal fibrosis (fibrosis of the soft tissue of the mediastinum), morphea, multifocal fibrosclerosis, myelofibrosis (fibrosis of the bone marrow), nephrogenic systemic fibrosis (fibrosis of the skin), nodular subepidermal fibrosis, pleural fibrosis, fibrosis as a consequence of surgery, proliferative fibrosis, pipestem fibrosis, postfibrinous fibrosis, progressive massive fibrosis (a type of fibrosis of the lungs, a complication of coal workers' pneumoconiosis), old myocardial infarction (fibrosis of the heart), pancreatic fibrosis, progressive massive fibrosis, radiation fibrosis, renal fibrosis, renal fibrosis related to or arising from fibrosis related to chronic kidney disease, retroperitoneal fibrosis (fibrosis of the soft tissue of the retroperitoneum), scarring after surgery, scleroderma/systemic sclerosis (fibrosis of the skin), subepithelial fibrosis, uterine fibrosis, and viral hepatitis induced fibrosis.

18. The method of claim 17, wherein the compound of Formula (I) is of Formula (IA)

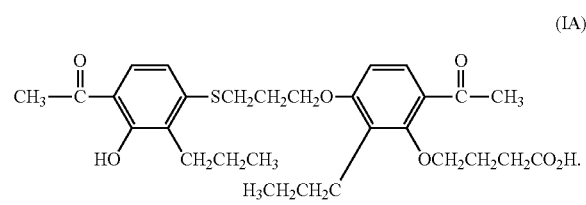

(IA)

19. The method of claim 17, wherein the metabolite of the compound of Formula (I) is a compound of Formula (IB):

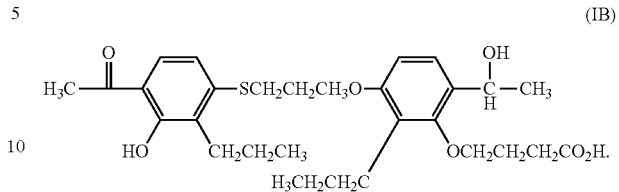

(IB)

20. The method of claim 17, wherein the compound is administered orally.

21. The method of claim 20, wherein the compound is administered as a tablet or a capsule.

22. The method of claim 18, wherein the compound is present in an orthorhombic polymorphic form A.

23. The method of claim 17, wherein the compound is administered as a liquid dosage form.

24. The method of claim 17, wherein the compound is administered in an amount from about 100 to about 4,000 mg/day, divided into one, two, or three portions.

* * * * *